US006004324A

United States Patent [19]

Gahr et al.

[11] Patent Number: 6,004,324

[45] Date of Patent: Dec. 21, 1999

[54] ADJUSTABLE LOCKING NAIL

[75] Inventors: Ralf Herbert Gahr; Hans Erich Harder, both of New York, N.Y.

[73] Assignee: Howmedica GmbH, Germany

[21] Appl. No.: 08/975,826

[22] Filed: Nov. 21, 1997

[51] Int. Cl.$^6$ .................................................... A61B 17/56

[52] U.S. Cl. ................................ 606/67; 606/66; 606/65; 606/62; 606/64

[58] Field of Search ................................ 606/67, 66, 65, 606/62, 64, 60, 68, 63

[56] References Cited

U.S. PATENT DOCUMENTS

| | | | |
|---|---|---|---|
| 4,628,919 | 12/1986 | Clyburn . | |
| 4,805,607 | 2/1989 | Engelhardt et al. | 606/67 |
| 5,041,114 | 8/1991 | Chapman et al. | 606/67 |
| 5,112,333 | 5/1992 | Fixel | 606/62 |
| 5,505,734 | 4/1996 | Caniggia et al. | 606/63 |
| 5,562,667 | 10/1996 | Shuler et al. | 606/64 |
| 5,569,249 | 10/1996 | James et al. | 606/62 |
| 5,653,709 | 8/1997 | Frigg | 606/62 |

FOREIGN PATENT DOCUMENTS

| | | |
|---|---|---|
| 03036709 | 3/1989 | European Pat. Off. . |
| 0506420 | 9/1992 | European Pat. Off. . |
| 0689800 A2 | 1/1996 | European Pat. Off. . |
| 2717371 | 9/1995 | France . |
| 3347055 | 12/1986 | Germany . |
| 3921972C2 | 6/1994 | Germany . |
| 668692 | 1/1989 | Switzerland . |
| WO9427514 | 6/1993 | WIPO . |
| 95/11635 | 5/1995 | WIPO . |
| 96/02201 | 2/1996 | WIPO . |
| 96/02203 | 2/1996 | WIPO . |
| 96/13220 | 5/1996 | WIPO . |

OTHER PUBLICATIONS

European Search Report dated Jun. 12, 1998.

*Primary Examiner*—Michael Buiz
*Assistant Examiner*—Tan-Uyen Thi Ho
*Attorney, Agent, or Firm*—Lerner, David, Littenberg, Krumholz & Mentlik, LLP

[57] ABSTRACT

A locking nail for placement in the marrow space of tubular bones for the care of bone fractures, with an elongate, essentially cylindrical shank with a number of essentially radial openings for accommodating locking screws. At least one radial, elongate opening extends in the longitudinal direction of the shank and at least two sliding blocks are unrotatably guided within the shank and are secured against a movement away from one another so that at least one opening at an angle to the longitudinal direction is formed from at least one intermediate space between the sliding blocks. This opening is aligned to the elongate opening for accommodating a locking screw. In another embodiment, only one such sliding block is used (and can be selected from any of a suitable set, for example a set in which the blocks of the set all have substantially the same length but have transverse bores positioned at a variety of different positions and at different angles with respect to the longitudinal axis of the nail).

14 Claims, 1 Drawing Sheet

ADJUSTABLE LOCKING NAIL

BACKGROUND OF THE INVENTION

The invention relates to locking nails.

Marrow nails and special locking nails are known aids for osteosynthesis. They are introduced into the marrow space of a damaged bone in order mechanically to bridge the bone lesion. With locking nails, locking screws (which are mounted transversely through the bone and through the locking nail) serve to secure the connection between the bone and locking nail against displacement in the direction of the bone axis and against rotation about the bone axis.

Until now, with usual locking nails, locking screws are placed in discrete openings and are arranged essentially radially in the locking nail. On the proximal thigh, for example, the screws are arranged also at an angle inclined to the shank axis. But in each case with respect to the length of the shank as well as with respect to the angle to the shank, they are not adjustably arranged.

An object of this invention is a locking nail in which the position or the angle of the opening in the locking screw can be changed and the locking screw can be adjustably located within the opening.

A further object is to be able to adjust the openings on locking nails for the locking screws according to position and angle, in order to adapt them to the individual situation in different patients, without having to prepare an assortment of complicated and expensively manufactured locking nails with differing arrangements of the openings for the locking screws.

These and other objects are achieved by the locking nail of the present invention.

SUMMARY OF THE INVENTION

According to the invention, a locking nail has at least one region in which locking screws are to be placed. There, in that region, an elongate opening passes radially through the shank of the locking nail and extends in the longitudinal direction of the shank. At least two sliding blocks (in a first embodiment) are nonrotatably guided and are secured against movement from one another within that opening. For accommodating a locking screw, an opening is formed from at least one intermediate space between the sliding blocks, which is aligned to the elongate opening, so that an opening radially passing through the nail arises for a locking screw. In a preferred embodiment of the invention the sliding surfaces of the sliding blocks (which are aligned to the intermediate space and limit the intermediate space) are concave and are adapted to the cylindrical form of the locking screws placed in this opening. The sliding blocks are guided within the shank in the elongate opening preferably by means of a positive fit. In a preferred embodiment of the invention, the sliding blocks comprise radial projections which engage into the elongate opening and which essentially occludingly fill out these openings with the outer contour. Also in the longitudinal direction of the shank, the elongate opening is essentially filled out by any selected number of sliding blocks, which are prevented from movement away from one another for example by a closure at the end of the elongate opening. In a preferred embodiment of the invention, the closure is formed by a closure screw which also may be employed for adjusting the width of the intermediate spaces between the sliding blocks for flush accommodation of locking screws of differing diameters; the closure screw occludes an opening, axial with respect to the shank, of the elongate opening at the end of the locking nail, wherein the elongate opening up towards this end extends over preferably a third of the length of the locking nail. At the same time the elongate opening may be located at the proximal and/or distal end of the locking nail. Every end of the locking nail provided with an elongate opening, in this preferred embodiment of the invention, may be provided with a ring which surrounds the locking nail in order to prevent the spreading out of the end of the shank. In this embodiment, the ring leaves the axial opening free for introducing the sliding blocks. Also, each elongate opening may be preferably formed as a slot extending in the longitudinal direction of the shank and radially passing through up to the end of the locking nail. The shank (at least in the region of the slot) is formed cylindrically hollow so that the sliding blocks may be guided with a positive fit in the hollow cylindrical inner contour of the shank.

With the help of the present invention a locking nail may be adapted before implantation to the individual anatomical or pathological situation of a patient; for the locking screws which are to run through the locking nail at a certain position and a certain angle corresponding to the patient's requirements, openings are placed and adjusted at a suitable position and at a suitable angle.

By using selected sliding blocks, one can achieve a selected number of openings, selected angles of the openings with respect to the longitudinal direction of the shank, and selected distances between the openings and the end of the locking nail. With this embodiment, each elongate opening is so filled out with a length and angle corresponding to the sliding blocks in the sliding surface that there arise intermediate spaces of a desired number, position and alignment.

DESCRIPTION OF THE PREFERRED EMBODIMENTS

BRIEF DESCRIPTION OF THE DRAWINGS

A preferred embodiment of the invention is described in the following by way of the appended drawings in which.

DETAILED DESCRIPTION OF THE DRAWINGS

Figure 1:
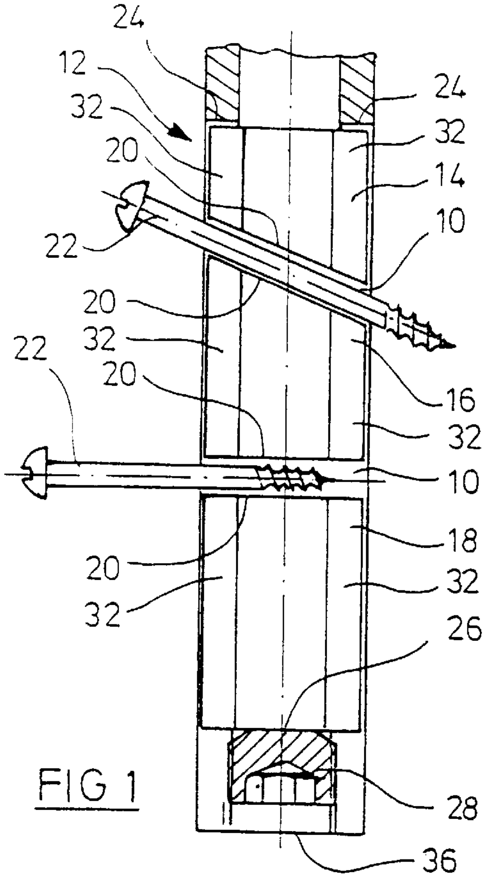
FIG. 1 shows a partial cross section in a lateral view through a shank end of a locking nail according to the invention, and including locking screws.
Figure 2:
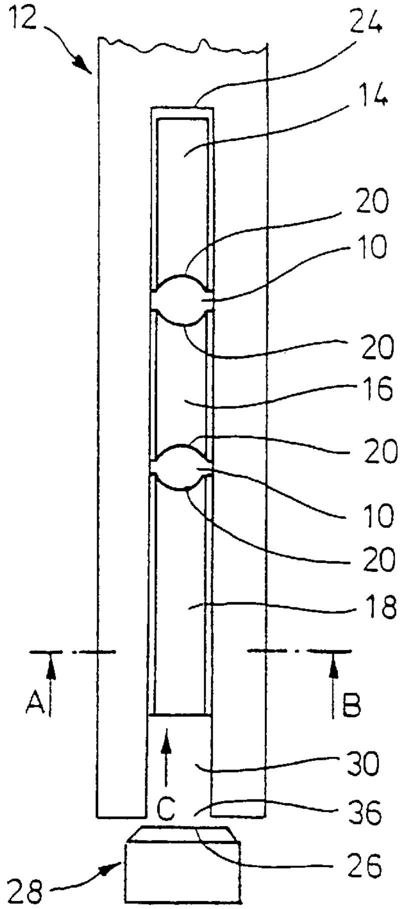
FIG. 2 shows a partial plan view of the same end as in FIG. 1 of the locking nail, without showing locking screws with an open closure.

Referring to FIGS. 1 and 2, in FIG. 2 two openings 10 near the end of a shank 12 of a locking nail are shown. Openings 10 are formed from the intermediate spaces between three sliding blocks 14, 16 and 18. The sliding surfaces 20 are concave and are aligned towards the openings 10 and limit the openings 10. FIG. 1 shows locking screws 22 positioned within the openings 10. The locking screws 22 are guided in their direction by the sliding surfaces 20 of the sliding blocks 14, 16 and 18 (See FIG. 4). The distances between the openings 10 (and thus between the locking screws 22) and the distance to the end of the locking nail is fixed by the lengths of the sliding blocks 14, 16 and 18. The angle that the openings 10 (or the locking screws 22) make with the longitudinal axis of the nail is determined by the angle of the sliding surfaces 20. In this embodiment, the sliding blocks 14, 16, 18 are secured against movement away from one another by stops 24 and by an adjustable stop of a closure screw 28.

Figure 3:
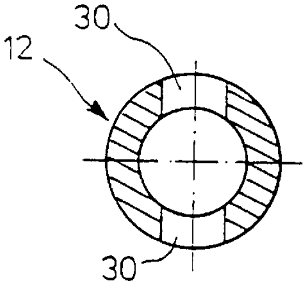
FIG. 3 shows a cross-section through the shank end taken along line A—A in FIG. 2 without sliding blocks.
Figure 4:
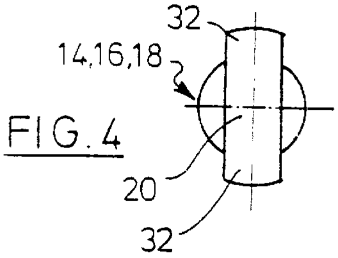
FIG. 4 shows a plan view of a sliding block as also shown in FIG. 2 in the direction of arrow C.

With reference to FIGS. 3 and 4, in FIG. 3 the hollow cylindrical shape of the shank 12 can be seen. In the radially extending elongate axial opening 30, the radial projections 32 of the sliding blocks 14, 16 or 18 are accommodated, and the sliding blocks are thus nonrotatably guided by means of a positive fit.

Again referring to FIGS. 1 and 2, the elongate opening 30 extends from the stops 24 in the longitudinal direction of the shank up to its end 36. With this, FIG. 1 shows that the radial projections 32 of the sliding blocks 14, 16 and 18 essentially occlude with the outer contour of the shank 12. The elongate opening 30 is essentially filled out by the sliding blocks 14, 16 and 18 in the longitudinal direction of the shank 12. The width of the intermediate spaces between the sliding blocks 14, 16 and 18 may be adjusted by turning the closure screw 28 upwards or downwards in the longitudinal direction of the shank 12.

FIG. 2 shows that the closure screw 28 is rotated out from the end of the shank 12 so that the sliding blocks 14, 16 and 18 may be exchanged with another set of sliding blocks (not shown) with the same cross section as is shown in FIG. 4. By way of the fact that with the second set of sliding blocks the intermediate spaces between the sliding surfaces are located at a different distance to one another and to the end of the shank 12, and the sliding surfaces are aligned at a different angle to the longitudinal direction of the shank 12, the openings 10 with respect to position and angle in the shank 12 may be adjusted by way of the geometry (length between the sliding surfaces, angle of the sliding surfaces to the longitudinal axis of the shank) of various sets of sliding blocks.

Figure 5:
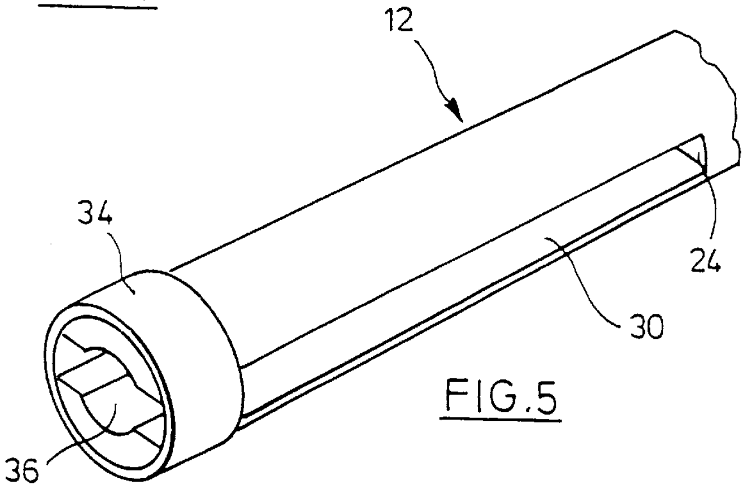
FIG. 5 shows a three-dimensional partial view of the same shank end as in FIGS. 1 and 2, with an additional ring, without showing locking screws, sliding blocks and closure.

FIG. 5 shows a ring 34 which surrounds the end of the shank 12 which is provided with an elongate opening 30, in order to prevent the spreading out of the shank end. With this the ring leaves an axial opening 36 free for introducing the sliding blocks 14, 16 and 18 with a cross section profile according to FIG. 4.

We claim:

1. A locking nail for placement in the marrow space of tubular bones for the care of bone fractures, with an elongate, essentially cylindrical shank with a number of essentially radial openings for accommodating locking screws, wherein at least one radial, elongate opening extends in the longitudinal direction of the shank and at least two sliding blocks are nonrotatably guided within the shank and are secured against movement away from one another so that at least one opening at an angle to the longitudinal direction is formed from at least one intermediate space between the sliding blocks, wherein said at least one opening is aligned with respect to the elongate opening for accommodating a locking screw.

2. A locking nail according to claim 1, wherein the sliding surfaces of the sliding blocks, aligned to the intermediate space, are concave.

3. A locking nail according to claim 2, wherein the sliding blocks are so formed within the shank that they are secured against radially falling out of the elongate opening by means of a positive fit.

4. A locking nail according to claim 3, wherein the sliding blocks comprise radial projections engaging into the elongate opening, which occlude essentially with the outer contour of the shank.

5. A locking nail according to claim 1, wherein said at least two sliding blocks comprise a set of exchangeable sliding blocks each having a different length in the longitudinal direction of the shank and a different angle between the sliding surface and the longitudinal direction of the shank.

6. A locking nail according to claim 5, wherein the elongate opening is essentially filled by any selected number of sliding blocks having the same or different lengths.

7. A locking nail according to claim 6, wherein the sliding blocks are secured against movement away from one another by means of a closure at the end of the locking nail.

8. A locking nail according to claim 7, and including also a closure screw.

9. A locking nail according to claim 8, wherein the width of the intermediate space between the sliding blocks can be set by adjusting at least one sliding block by means of an adjustable stop.

10. A locking nail according to claim 9, wherein the length of the elongate opening is at least one third of the length of the locking nail.

11. A locking nail according to claim 10, wherein an elongate opening is located near at least one end of the locking nail.

12. A locking nail according to claim 11, wherein said elongate opening located near at least one end of the locking nail is formed by a slot which extends in the longitudinal direction of the shank and extends radially through said shank nearly to said end, wherein said shank at least near said slot is formed cylindrically hollow and wherein said sliding blocks are guided in said shank by means of a positive fit.

13. A locking nail according to claim 12, and including also a ring located near said slot, wherein said ring surrounds said locking nail and leaves free an axial opening for introducing therewithin said sliding blocks.

14. A locking nail for placement in the marrow space of tubular bones for the care of bone fractures, said nail having an elongate essentially cylindrical shank with a number of essentially radial openings for accommodating locking screws, wherein at least one radial opening extends in the longitudinal direction of the shank, wherein a set of single sliding blocks is provided, each single block adapted to be accommodated singly by said nail and nonrotably guided within said shank and secured against movement, each single block of said set having at least one traverse bore, with the axial position and the angle of the traverse bore being different and with the traverse bore being aligned with the elongate opening.

* * * * *

UNITED STATES PATENT AND TRADEMARK OFFICE

CERTIFICATE OF CORRECTION

PATENT NO. : 6,004,324
DATED : December 21, 1999
INVENTOR(S) : Gahr et al.

It is certified that error appears in the above-identified patent and that said Letters Patent is hereby corrected as shown below:

On the face of the patent:

In the "Inventors" section, "New York, N.Y." should read -- Fed. Rep. Germany --;

In between "[22] Filed: November 21, 1997 and [51] Int. Cl.$^6$.........A61B/17/56", insert:

-- [30] Foreign Application Priority Data

Nov. 22, 1996 Fed. Rep. Germany ................ 296 20 327.0 --

Signed and Sealed this

Twenty-fourth Day of April, 2001

Attest:

NICHOLAS P. GODICI

*Attesting Officer* *Acting Director of the United States Patent and Trademark Office*